(12) United States Patent
Zakoshansky et al.

(10) Patent No.: US 6,331,654 B1
(45) Date of Patent: Dec. 18, 2001

US006331654B1

(54) METHOD OF PRODUCTION OF PRODUCT ACETONE OF HIGH STABILITY TO OXIDATION

(75) Inventors: Vladimir Mikhailovitch Zakoshansky, Mt. Vernon, IN (US); Irina Ivanovna Vassilieva, St. Petersburg (RU)

(73) Assignee: Illa International LLC, Reno, NV (US)

( * ) Notice: Subject to any disclaimer, the term of this patent is extended or adjusted under 35 U.S.C. 154(b) by 0 days.

(21) Appl. No.: 09/501,647

(22) Filed: Feb. 10, 2000

(51) Int. Cl.$^7$ .................................................. C07C 45/83
(52) U.S. Cl. .................. 568/411; 568/385; 568/410; 568/798
(58) Field of Search ................................. 568/385, 410, 568/411, 798

(56) References Cited

U.S. PATENT DOCUMENTS

| | | | |
|---|---|---|---|
| 3,668,256 | * | 6/1972 | Brundege ..................... 260/593 P |
| 4,329,510 | * | 5/1982 | Uno et al. ........................... 568/411 |
| 4,340,447 | * | 7/1982 | Laverick et al. ................... 203/36 |
| 4,626,600 | * | 12/1986 | Fulmer et al. ..................... 568/411 |
| 4,722,769 | * | 2/1988 | Chan et al. ......................... 203/30 |
| 5,399,776 | * | 3/1995 | Fraini et al. ....................... 568/411 |

FOREIGN PATENT DOCUMENTS

0190790 * 8/1986 (EP) .

* cited by examiner

*Primary Examiner*—Sreeni Padmanabhan
(74) *Attorney, Agent, or Firm*—Edward Etkin, Esq

(57) ABSTRACT

Disclosed is a method for the production of product acetone of higher oxidation stability where the product acetone is produced by a multi-step rectification process in the presence of alkali catalyst. The embodiments of the method of present invention utilize a two-column and a one-column scheme of product acetone rectification from an acetone stream. In a two-column embodiment of the present invention, acetone is taken off in a vapor phase as a side-draw in a first column and directed to a partial condenser wherein it is separated into liquid and vapor phases with a simultaneous feed of aqueous sodium hydroxide solution to the first column above the feed tray. The vapor phase of the partial condenser is forwarded to a second column where the product acetone is rectified and then removed overhead, the bottom products are recycled to the first column feed, and the liquid phase of the partial condenser is treated with alkali and recycled either to the first column or to a neutralization stage of cumene hydroperoxide cleavage products. In a one-column embodiment of the present invention, acetone is taken off in the vapor phase overhead and directed to the partial condenser with the simultaneous feed of the aqueous sodium hydroxide solution above the feed tray. Product acetone is then condensed from the vapor phase and removed.

25 Claims, 2 Drawing Sheets

METHOD OF PRODUCTION OF PRODUCT ACETONE OF HIGH STABILITY TO OXIDATION

BACKGROUND OF THE INVENTION

This invention relates to the field of the manufacturing of synthesis commercial petrochemical products, and, in particular, to the process of the production of acetone which is commonly used as a solvent and reagent.

The conventional method of the commercial acetone production is a liquid phase cumene oxidation to cumene hydroperoxide with further cleavage of cumene hydroperoxide to phenol and acetone. The oxidation products contain, among the desired products, carbonyl by-products and, in particular, aldehydes. The acetone treatment of aldehydes is difficult. The presence of carbonyl compounds worsens the quality characteristics of the product acetone, namely, greatly decreasing such characteristics as the acetone stability to oxidation with potassium permanganate (the permanganate test).

U.S. Pat. No. 4,885,399 teaches a method to treat ketones from aldehydes through a Tishchenko reaction conducted in the presence of weak Lewis acids. However, a disadvantage of this method is the requirement of a careful preliminary drying of the product or of a synthesis in a special solvent, that complicates the process scheme and makes it more expensive.

Another approach is taught by U.S. Pat. No. 5,399,776. In accordance with the '776 patent, acetone is treated by binding the aldehyde impurities contained in acetone to various diamines followed by distillation of the treated product. However, a disadvantage of this method is that the chemical reagents needed for the treatment are expensive, and the ammonia compounds produced in the reaction have a negative environmental impact.

The most commonly used previously known method to treat acetone from aldehydes is treatment of crude acetone in the presence of an alkaline catalyst based on the reaction of their condensation to form aldoles. Variations of this approach are disclosed in U.S. Pat. Nos. 4,626,600, 4,722,769, and 4,340,447. Each of these patents discloses different process scheme of product acetone rectification in the presence of alkali catalyst.

The '600 patent describes the scheme of the product acetone rectification where the reaction cleavage products containing acetone, phenol, cumene, α-methylstyrene, water, products of phenol and α-methylstyrene condensation and impurities are introduced to a rectification column. The main purpose of this column is to separate the reaction cleavage products into acetone and phenol streams. An overhead acetone stream containing acetone, cumene, water and α-methylstyrene is delivered to a product acetone rectification stage. The rectification of product acetone from the acetone stream is made in two columns. In the first column, only the aldehyde fraction and small acetone recycle flow directed to a CHP cleavage stage are distilled. The entire acetone stream is then delivered to a product acetone column wherein the product acetone is received overhead with a reflux ratio above 5 (the reflux ratio can be reduced to 2.5 in highly efficient columns filled with such packings as Intalox-2T). The bottom products which are a heterogeneous mixture of cumene, α-methylstyrene and water are delivered to a phase separator. The hydrocarbon fraction from the separator is delivered to further treatment. The water phase is delivered to a neutralization stage of CHP cleavage products. The aqueous alkaline solution is introduced to the neutralization stage with the feed but more often above the feed point (in highly efficient columns filled in with the packings like Intalox-2T it is preferable to feed the aqueous alkali solution only with the feed due to poor alkali solubility in acetone).

The main disadvantage of the scheme of the '600 patent is that the product acetone has low stability to oxidation (a permanganate test shows no more than 4 hours) due to the reversibility of a aldole condensation reaction. Research has shown that aldehydes in the acetone stream containing cumene and water are distributed between organic and water phases at a weight ratio of 2:1. When the acetone stream is treated with the aqueous alkaline solution, aldehydes contained in the water phase do not enter into the aldole condensation reaction. However, aldehydes contained in the organic phase enter easily into the aldole condensation reaction. The majority of the aldole condensation products enter the water phase. Accordingly, the water phase of the acetone stream contains free aldehydes and aldole condensation products. When the acetone stream treated with alkali is rectified at elevated temperatures, the aldole condensation products are partially decomposed. As a result, aldehydes enter the final product. Therefore, the permanganate test of product acetone does not usually exceed 4 hours. At a low efficiency of product acetone rectification column, small amounts of the aldole condensation products enter the final product, decreasing the permanganate test value in addition to the action of the aldehydes.

The '769 patent discloses a scheme of product acetone rectification. This scheme differs from the one taught by the '600 patent as follows: in the '769 patent, the product acetone is rectified with the use of only one rectification column. The reaction cleavage products are delivered to the rectification column, as in the '600 patent, where the acetone stream containing acetone, cumene, water and α-methylsterene is overhead rectified and then directed to the product acetone column. The acetone stream to the column is introduced as vapor and liquid phases. Aqueous alkali solution is added above the feed point. The product acetone in a liquid phase is removed as a side-draw, the distillate is condensed and its part returns to the column between the feeding and the introduction of the aqueous alkaline solution. The '769 patent insists that for the process to be successful, the optimum regime should remain in the column by controlling the temperature profile because the main aldehyde-alkali interaction proceeds on the trays where simultaneous water and hydrocarbon phases are present. Since the side draw of product acetone is conducted as a liquid phase, the required amount of the liquid on a drawoff tray can be provided for only by large recycle streams due to large reflux stream. A column of large diameter is needed for such a process. Therefore, the energy consumption increases due to the large recycle flows. The '769 patent admits that a disadvantage of the invention disclosed therein is the limitation of the cumene content in the acetone stream. As shown in the patent, the cumene content in the acetone stream cannot exceed 4 wt % in order to produce acetone product of required quality. In many commercial processes the cumene content in the acetone stream is much higher than 4 wt % and commonly reaches 17–20 wt %.

The '447 patent teaches the scheme of product acetone rectification similar to the scheme disclosed in the '769 patent. However, the arrangement disclosed in '447 patent differs from the one taught in the'769 patent in that the acetone stream in the vapor phase containing acetone, water and aldehyde impurities is delivered from the rectification column through a partial condenser to a product acetone column. The phase condensed in the partial condenser is delivered to the rectification column as a reflux. The cumene content in the acetone stream is not provided. The acetone stream is delivered to the product acetone rectification column where the product acetone is rectified as a side-draw. The distillate is condensed and its part is introduced to the reflux flow in the column overhead. The other part of the distillate is introduced to a stage of technical hydroperoxide cleavage. The aqueous alkaline solution in the product acetone column is introduced above the feed point. The alkaline concentration may vary from 0.01 to 5.0 wt. %. The pressure in the product acetone rectification column overhead is kept within the range 0.3–0.8 bars, a temperature in the bottom is kept within the range 80–120□□. The weight ratio of the reflux flow to the side-draw flow ranges from 4:1 to 25:1.

According to the schemes taught by the '769 and '447 patents, acetone of high oxidation stability cannot be produced for the above mentioned reasons. When product acetone is rectified by the schemes described in the '600, '769, and '447 patents, the energy consumption is high due to high reflux ratio.

Therefore it would be desirable to eliminate the said disadvantages and to produce product acetone with higher oxidation stability with the use of the product acetone rectification in the presence of an alkaline catalyst.

SUMMARY OF THE INVENTION

The object of the present invention is to eliminate the above-described disadvantages of previously acetone production methods, and to produce acetone with a higher stability to oxidation. In brief summary, in accordance with the inventive process, product acetone is obtained through a multi-step rectification process in the presence of alkali catalyst.

Disclosed is a method for the production of product acetone of higher oxidation stability with potassium permanganate (permanganate test shows above 10 hours) where the product acetone is produced by a multi-step rectification process in the presence of alkali catalyst. The embodiments of the method of present invention utilize a two-column and a one-column scheme of product acetone rectification from an acetone stream containing acetone, cumene (to 30 wt %), water (to 20 wt %), (α-methylsterene and aldehyde impurities. The rectification columns operate either under atmospheric pressure or at a vacuum of 400–650 mm Hg. To produce product acetone of higher stability to oxidation containing below 100 ppm of aldehydes, the amount of fed alkali catalyst is varied. In order to avoid the penetration of aldole condensation products into product acetone, which in addition to aldehydes decreases the value of the permanganate test, the acetone is taken off in a vapor phase and directed to a partial condenser where the degree of removal of aldole condensation products is obtained as 90% by varying a weight ratio of vapor and condensed flows.

In a two-column embodiment of the present invention, acetone containing 1–2 wt % of acetone is taken off in the vapor phase as a side-draw in a first column and directed to the partial condenser wherein it is separated into liquid and vapor phases at a flow ratio ranging from 1:10 to 1:100, respectively, with a simultaneous feed of aqueous sodium hydroxide solution to the first column above the feed tray based on 100% NaOH from about 0.036 ton to 0.06 ton per 1 ton of acetone depending on the required value of the permanganate test from 10 to 70 hours. The vapor phase of the partial condenser is forwarded to a second column where the product acetone is rectified overhead at a reflux ratio not higher than 2.5, and the bottom products, which are the aqueous acetone solution containing 30–40 wt % of water, are recycled to the first column feed. The liquid phase of the partial condenser is treated with alkali and recycled either to the first column or to a neutralization stage of cumene hydroperoxide cleavage products.

In a one-column embodiment of the present invention, acetone is taken off in the vapor phase overhead and directed to the partial condenser at the ratio of liquid and vapor phases ranging from about 1:50 to 1:150 with the simultaneous feed of the aqueous sodium hydroxide solution above the feed tray on the basis of 100% NaOH from about 0.0036 ton to 0.006 ton per 1 ton acetone, depending on the required value of the permanganate test from 4 to 40 hours.

Research has shown that product acetone should contain aldehydes below 5–10 ppm and almost no aldole condensation products to ensure that acetone has high stability to oxidation (the permanganate test above 10 hours). In order to produce product acetone with such characteristics, the amount of alkaline catalyst shall be varied. In order to avoid the penetration of aldole condensation products into product acetone, acetone must be taken off as a vapor phase to the partial condenser where the degree of the removal of aldole condensation products is 90% due to the change of weight ratio of vapor and condensed streams.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

In the drawing, wherein like reference characters denote corresponding or similar elements throughout the figure.

DESCRIPTION OF THE PREFERRED EMBODIMENT

The present invention is aimed at eliminating the disadvantages of previously known acetone production processes and at improving the stability of product acetone to oxidation. In accordance with the present invention, high stability to oxidation with regard to desired product acetone is achieved.

The present invention is intended to operate as part of a complete process for production of acetone. Accordingly, certain well-known process stages, such as neutralization and treatment, that may occur before, during, and after the inventive process, are referred to below but not described in detail. Furthermore, it should be understood that in describing embodiments of the process of the present invention, varying quantities of products, impurities and agents are used by way of illustrative examples only and are not intended to serve as limitations for the inventive process other than as recited in the appended claims.

Figure 1:
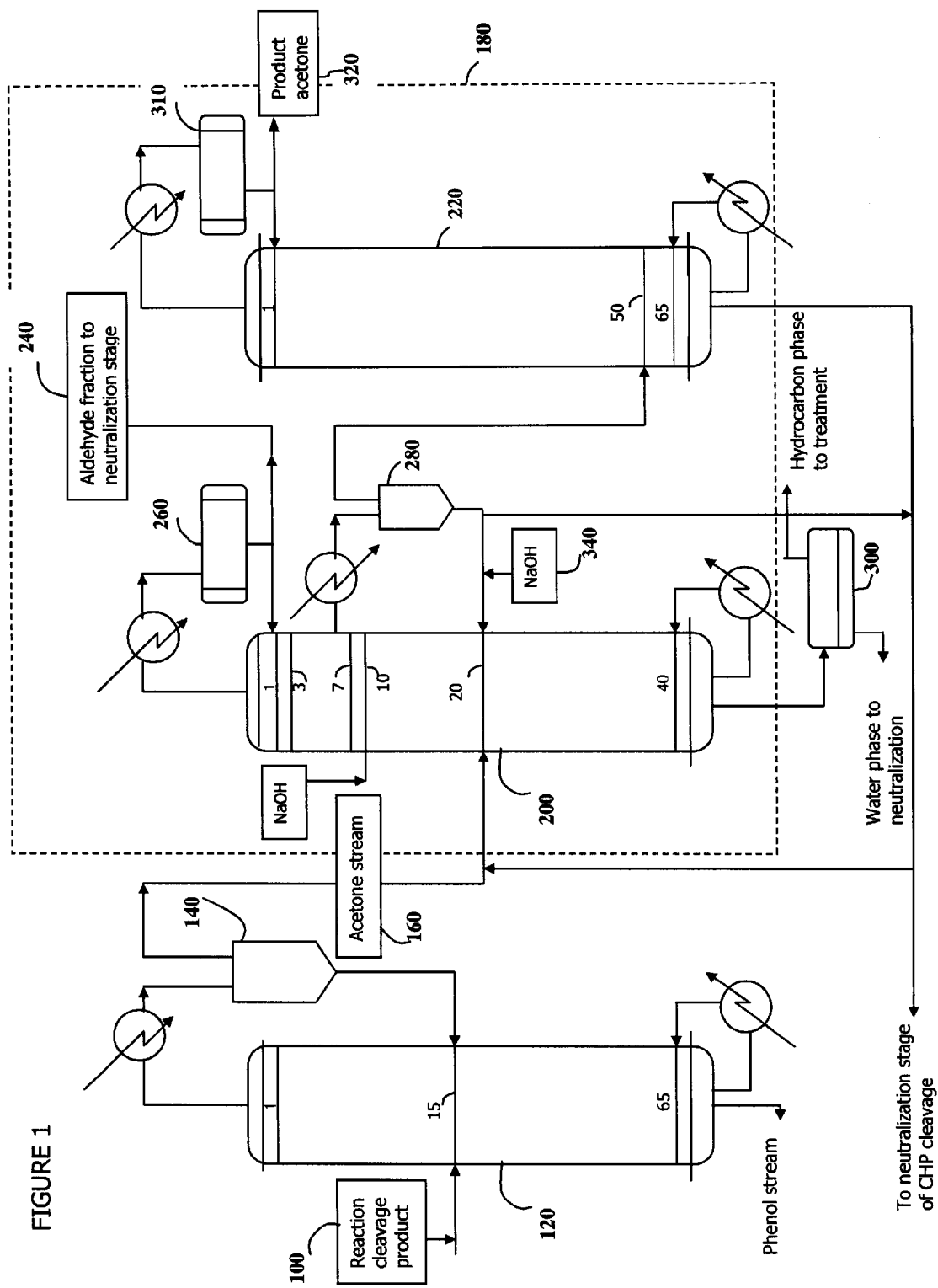
FIG. 1 schematically shows a first embodiment of the process of the invention where two rectification columns are utilized.

In a first embodiment of the present invention, two rectification columns are utilized. Referring now to FIG. 1 reaction cumene hydroperoxide cleavage products 100 are delivered to a first rectification column 120 where separation into acetone and phenol streams occurs. Preferably, column 120 operates at an atmospheric pressure, but it can also be operated under a vacuum of 760–600 Hg mm. An acetone stream 160 is taken off overhead in the column 120. Preferably, the acetone stream 160 is taken off in a vapor phase and supplied to a partial condenser 140. The mass ratio of the vapor and condensed streams through the partial condenser 140 is maintained within the range of about 1:0.02 to about 1:0.1. The vapor phase from the partial condenser containing acetone, cumene (up to 40 weight %), water (up to 20 weight %) and α-methylstyrene, is delivered to a product acetone rectification stage 180 consisting of two rectification columns 200 and 220, each containing a number of trays, that are operated either under atmospheric pressure or under vacuum 400–600 mm Hg as a matter of design choice. Preferably, the column 200 is operated under atmospheric pressure while the column 220 is operated under vacuum. The condensed phase is delivered to the column 120 upper tray. From about 2 to about 10 weight % relative products are condensed in the partial condenser 140.

In an alternate embodiment of the invention, the condenser 140 is configured as a total condenser and the acetone stream 160 is taken off in a liquid phase and then directed to the total condenser 140. When the acetone stream 160 is taken off in a liquid phase, the reflux ratio in the column 120 is maintained within the range of about 2–0.7, and preferably about 1–0.7. The acetone stream 160 in the liquid phase containing acetone, cumene (to 40 weight %), water (to 20 weight %) and α-methylstyrene then enters the product acetone rectification stage 180.

In the rectification column 200, an aldehyde fraction 240 is removed overhead through a second total condenser 260 and delivered to a neutralization stage (not shown). From trays 3 to 7 all the acetone is removed as a side-draw though a second partial condenser 280 in a vapor phase containing about 1–2 wt % water. At the same time, an aqueous sodium hydroxide solution 330 is fed to the rectification column 200, to approximately tray 10 above a feed tray 20, based on 100% NaOH from about 0.036 ton to 0.06 ton per 1 ton of acetone (depending on the required permanganate test value from 10 to 70 hours). Hydrocarbons and water are removed as bottom products, and split at vessel 300 into a hydrocarbon phase which is delivered to a treatment stage (not shown) and a water phase which is delivered to the neutralization stage (not shown).

The side-draw products coming as a vapor phase to the partial condenser 280 are separated there to liquid and vapor phases at the weight ratio of flows from 1:10 to 1:100, respectively. The vapor phase of the partial condenser 280 is directed to the rectification column 220 where product acetone 320 is removed overhead through a third total condenser 310 at a reflux ratio not above about 2.5. The bottom products of the column 220, which are the liquid acetone solution containing 30–40 wt % water, are returned to the feed of the column 200. The liquid phase of the partial condenser 280 is treated with alkaline 340 to be recycled either to the second column or to the neutralization stage of cumene hydroperoxide cleavage (not shown).

When the process of product acetone production is conducted in accordance with the above-described embodiment, almost complete removal of aldehydes from the vapor is achieved by feeding alkali 330 above the feed tray 20 in the column 200. However, in case the aldehydes are not completely removed, the removal process will be completed in the column 220 overhead third total condenser 310. The side draw products, drawn through the partial condenser 280, will contain minimum aldehydes. If the aldehyde content in the side-draw products exceeds 10 ppm and also if this stream contains aldole condensation products, then the content of aldehydes and aldole condensation products in product acetone can be compensated for by varying the weight ratio of the vapor and liquid phases in the partial condenser 280. If the inventive process is conducted in accordance with the embodiment shown in FIG. 1, the purpose of the column 220 is to separate acetone and water. As shown by research, calculations and commercial experience, the reflux ratio in the column 220 should not exceed 2.5 in order to provide the required water content in product acetone (water content in product acetone should not exceed 0.4 wt %).

Figure 2:
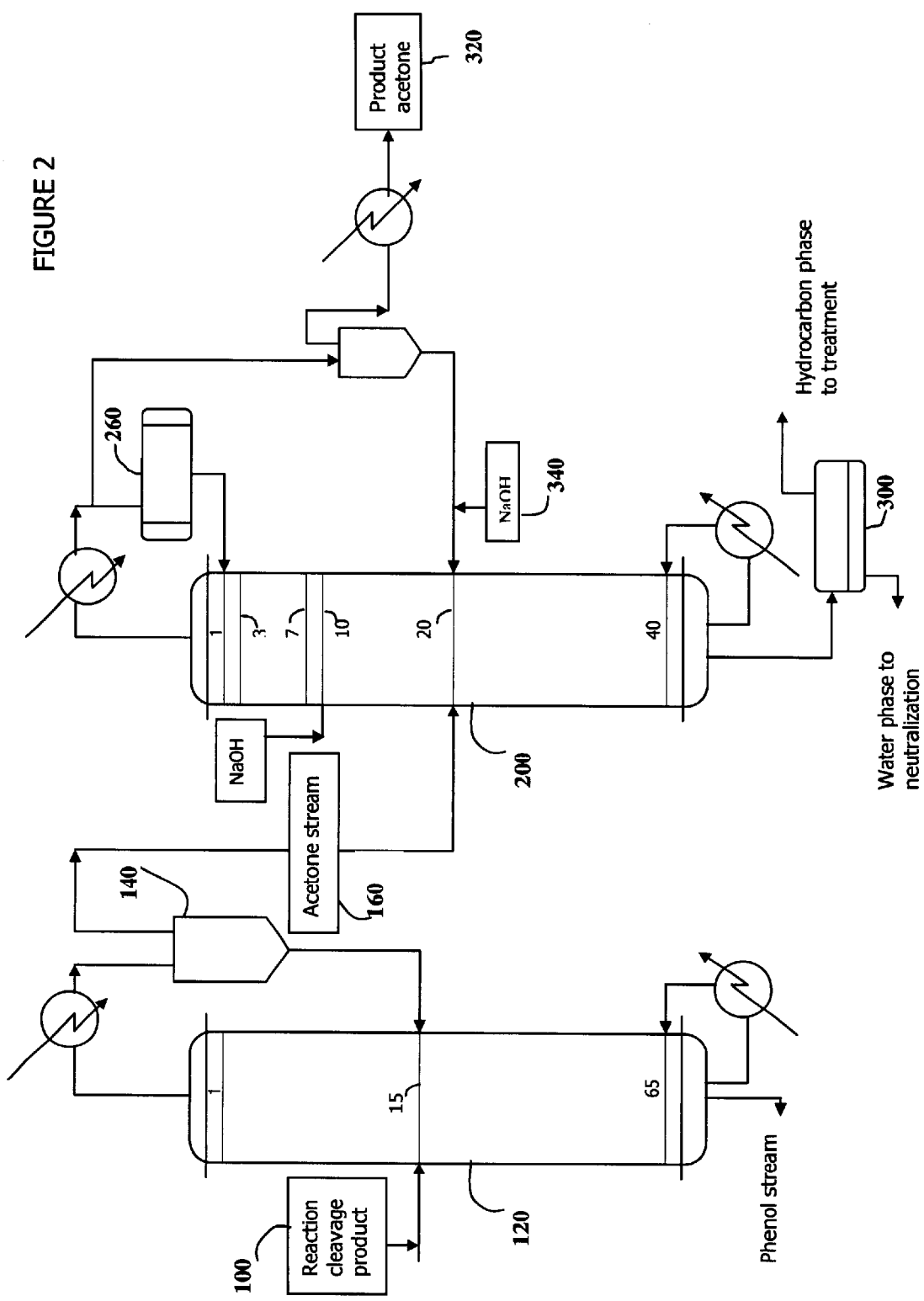
FIG. 2 schematically shows a second embodiment of the process of the invention where one rectification column is utilized.

Referring to FIG. 2, according to research and experimentation, acetone removed as a side product can be obtained without aldehydes by varying the alkali catalyst 330 flow rate. If the pressure in the column 200 is kept below the atmospheric pressure, the water content in the distillate is decreased at a constant reflux ratio. In this case, a single column 200 can be used to rectify product acetone rather than two columns 200 and 220 shown in FIG. 1. Accordingly, FIG. 2 shows a second embodiment of the present invention, where a single column 220 is utilized at the product acetone rectification stage to produce product acetone with high stability to oxidation.

In FIG. 2, the acetone stream 160 containing acetone, cumene (to 40 wt. %), water (to 20 wt. %) and α-methylsterene is directed to the rectification column 200 where acetone containing not less than about 1 wt % of water is removed overhead, through the second total condenser 260, as a vapor phase and directed to the partial condenser 280 to be separated at a liquid phase to vapor phase ratio from 1:50 to 1:150. Simultaneously, aqueous sodium hydroxide 330 is introduced above the feed tray 20 based on 100% NaOH in an amount from 0.036 ton to 0.06 ton per 1 ton acetone, depending on the required permanganate test value from 4 to 40 hours. The vapor phase of the partial condenser 280 is condensed to produce final acetone 320. The liquid phase of the partial condenser 280 is treated with aqueous alkali solution. Then the formed crude acetone is recycled to the column 200 to the feed point above the feed tray 20 or to the reflux above the tray 1.

The advantageous features (and differences with respect to previously known approaches) of the process of the present invention are best illustrated by the following comparison with the most superior of the previously known processes disclosed in the '447 patent:

1. The cumene content in the acetone stream delivered to product acetone rectification ranges from 1 to 40 wt %;
2. The water content in the acetone stream delivered to product acetone rectification ranges from 2 to 20 wt %;
3. An aldehyde content in product acetone below 10 ppm is achieved by varying the alkali catalyst flow rate above the feed point (weight ratio of 100% NaOH to acetone is from about 0.036 to 0.060);
4. The condensed products of the partial condenser, containing unreacted aldehydes, aldole and acetone, are additionally treated with an alkali catalyst and either recycled to the column or directed to the neutralization stage;
5. The degree of the aldole separation in the partial condenser exceeds 90%;
6. The acetone content of the bottom products of the column 200 containing hydrocarbons and water (see FIG. 1 or FIG. 2) does not exceed about 0.5 wt %;
7. Acetone is taken off from the column 200 (see FIG. 1 or FIG. 2) as a vapor phase to decrease the energy consumption;

8. The product acetone produced in accordance with the first and second embodiments of the present invention has a high stability to oxidation (the permanganate test value ranges from 10 to 70 hours).

The aforementioned advantages and features of the developed technology are demonstrated by Examples 1–5. The Examples are further summarized in a Table 1. The composition of the acetone stream, the alkali catalyst concentration, the number of feed trays and rectification product removal trays given in the examples are given by way of example only and are not intended to restrict or limit the scope or application of this invention in any way.

The comparative laboratory studies of product acetone rectification in accordance with the teachings of the '447 patent (Example 1) and in accordance with the embodiments of the present invention were made in a laboratory packing rectification column.

EXAMPLE 1

(Comparative by Prototype) in Accordance with the '447 Patent

The acetone stream containing acetone, water (3 wt %) and such impurities as acetaldehyde in an amount of 600 ppm, and phenol in amount of 3000 ppm was fed to the product acetone rectification column having 55 real trays. The diameter of the column was 38 mm. The feed rate was 200 ml/hr. The feed was introduced to a $45^{th}$ tray (the numeration of the trays was from the top of the column). The column overhead pressure was 450 mm Hg. The aqueous alkali solution (15% NaOH) was fed to a $35^{th}$ tray. The alkali flow rate was 3.5 ml/hr. The stream containing acetone and aldehyde was taken off overhead then condensed and returned to the reflux. The product acetone in the liquid phase was taken from the $10^{th}$ tray. The product acetone had a permanganate test value 4 hours. The reflux ratio (the ratio of overhead flow and the product acetone flow) was kept at 10:1. The column bottom products contained water, aldole condensation products, phenol, sodium phenate and acetone in the amount of 1 wt %. The steam consumption was 0.4 kg steam/kg acetone.

EXAMPLE 2

Experiment 2 was conducted in accordance with the first embodiment of the present invention shown in FIG. 1. The acetone stream containing acetone is (60 wt %), cumene (20 wt %), α-methylstyrene (3 wt %), water (17 wt %) and acetaldehyde impurities in an amount of 600 ppm and phenol in amount of 3000 ppm, was fed to the column 200. The column 200 had 40 real trays. The diameter of the column 200 was 28 mm. The feed rate was 200 ml/hr. The feed was introduced to tray 20. The column overhead pressure was atmospheric. The aqueous alkali solution (20% NaOH) was fed to the tray 10. The alkali flow rate was 2.4 ml/hr (on the basis of 100% NaOH–0.0048 gram NaOH per 1 gram acetone). The acetone stream containing 25 ppm of acetaldehyde (0.5 ml/hr) was taken off overhead through the second total condenser 260. The stream in vapor phase with flow rate 134 ml/hr was taken off from the tray 5. This stream contained acetone, water (1.5 wt %), acetaldehyde (15 ppm) and no aldole condensation products. The bottom products stream contained water, cumene, α-methylsterene, phenol and phenates. The acetone content of the bottom products did not exceed 0.3 wt %. The bottom temperature was kept no higher than 105°□. The acetone stream from the tray 5 in vapor phase was delivered to the partial condenser 280. The weight ratio of the vapor flow and condensed flow in the partial condenser 280 was kept at 1:100. The vapor flow from the partial condenser 280 containing acetone, water (1 wt %) and acetaldehyde (8 ppm) was then delivered to the column 200. Column 220 had 65 real trays. The diameter of the column 220 was 38 mm. The feed rate was 134 ml/hr. The feed was introduced to the tray 50 of the column 200. The overhead pressure of the column 220 was 600 mm Hg. The product acetone 320 was taken off overhead, through the third full condenser 310, from the column 220 with flow rate 120 ml/hr. The reflux ratio was kept at 2.5. The water content in product acetone was 0.3 wt %. The acetaldehyde content was 10 ppm. The permanganate test of product acetone 320 showed 40 hours. The bottom products of the column 220 containing acetone and water were returned to the feed of the column 200. The steam consumption was 0.25 kg steam/kg acetone.

EXAMPLE 3

Experiment 2 was conducted in accordance with the second embodiment of the present invention shown in FIG. 2. The acetone stream containing acetone (60 wt %), cumene (20 wt %), α-methylsterene (3 wt %), water (17 wt %) and acetaldehyde impurities in an amount of 600 ppm and phenol in an amount of 3000 ppm was fed to the column 200. The column 200 had 65 real trays. The diameter of the column was 38 mm. The feed rate was 200 ml/hr. The feed was introduced to the tray 32. The column overhead pressure was 600 mm Hg. The aqueous alkali solution (20% NaOH) was fed to tray 10. The alkali flow rate was 2.4 ml/hr (on the basis of 100% NaOH–0.0048 gram NaOH per 1 gram acetone). The acetone stream containing 15 ppm of acetaldehyde, 0.7 wt % of water and no aldole condensation products, was taken off overhead, through the second total condenser 260, in a vapor phase at flow rate of 133 ml/hr.

The bottom products contained water, cumene, α-methylsterene, phenol and phenates. The acetone content in the bottom products did not exceed 0.3 wt %. The bottom temperature was kept below about 105°□. The acetone stream from the column overhead was delivered to the partial condenser 280. The weight ratio of the vapor flow and condensed flow in the partial condenser 280 was kept at 1:150. The product acetone 320 was obtained by condensing the vapor phase from the partial condenser 280. The product acetone 320 contained 0.3 wt % of water and 100 ppm of acetaldehyde. The permanganate test of product acetone showed 30 hours. The steam consumption was 0.15 kg steam/kg acetone.

EXAMPLE 4

The process of product acetone rectification is conducted in the same manner as in Example 2, except that the flow rate of the alkali solution was 3.0 ml/hr (on the basis of 100% NaOH–0.006 gram NaOH per 1 gram acetone). The overhead pressure of the column 200 was kept at 600 mm Hg. The stream in the vapor phase was taken off from the tray 5 in the vapor phase at a flow rate of 133.5 ml/hr. This stream contained acetone, water (1.0 wt %), acetaldehyde (10 ppm) and no aldole condensation products. The acetone stream from the tray 5 was delivered in the vapor phase to the partial condenser 280. The weight ratio of the steam flow and condensed flow in the partial condenser was kept at 1:50. The vapor flow from the partial condenser 280 containing acetone, water 0.7 wt %, and acetaldehyde 6 ppm, was delivered to the column 200. The product acetone 320 was taken off, through the third total condenser 310, overhead from the column 230 at flow rate 120 ml/hr. The reflux ratio was kept at 2.0. The water content in product acetone was 0.3 wt %, the acetaldehyde content was 7 ppm. The permanganate test of product acetone showed 65 hours. The steam consumption was 0.26 kg steam/kg acetone.

EXAMPLE 5

The process of product acetone rectification is conducted in the same manner as in Example 3, except that the flow rate of the alkali solution was 3.0 ml/hr (on the basis of 100% NaOH–0.006 gram NaOH per 1 gram acetone). The column 200 overhead pressure was kept at 500 mm Hg. The acetone stream in the vapor phase was removed as overhead at a flow rate 132.7 ml/hr. This stream contains 10 ppm of acetaldehyde, 0.5 wt % of water and no aldole condensation products. The acetone stream from the column 200 overhead is delivered to the partial condenser 280. The weight ratio of the vapor flow and condensed flow in the partial condenser 280 was kept at 1:100. The product acetone 320 is obtained by condensing the vapor flow from the partial condenser 280. The product acetone 320 contained water at 0.3 wt % and acetaldehyde at 8 ppm. The permanganate test of product acetone showed 40 hours. The steam consumption was 0.16 kg steam/kg acetone.

TABLE 1

Example Summary Table

| Parameter | Example 1 | Example 2 | Example 3 | Example 4 | Example 5 |
|---|---|---|---|---|---|
| Feed rate, ml/hr | 200 | 200 | 200 | 200 | 200 |
| Acetaldehyde cintent in acetone stream, ppm | 600 | 600 | 600 | 600 | 600 |
| Consumption of 100% NaOH, g/g acetone | 0.0035 | 0.0048 | 0.0048 | 0.006 | 0.006 |
| Steam consumption, kg steam/kg acetone | 0.4 | 0.25 | 0.15 | 0.26 | 0.16 |
| Weight ratio of vapor and liquid flows in the partial condenser | | 1:100 | 1:150 | 1:50 | 1:100 |
| Permanganate test of product acetone, hr | 4 | 40 | 30 | 65 | 40 |

Thus, while there have shown and described and pointed out fundamental novel features of the invention as applied to preferred embodiments thereof, it will be understood that various omissions and substitutions and changes in the form and details of the devices and methods illustrated, and in their operation, may be made by those skilled in the art without departing from the spirit of the invention. For example, it is expressly intended that all combinations of those elements and/or method steps which perform substantially the same function in substantially the same way to achieve the same results are within the scope of the invention. It is the intention, therefore, to be limited only as indicated by the scope of the claims appended hereto.

We claim:

1. A rectification method, for producing high purity acetone from CHP cleavage products, implemented in a multi-stage process system, the system comprising a first, a second, and a third column, the method comprising the steps of;
    (a) producing an acetone fraction from a first column overhead, the first column functioning without reflux;
    (b) providing a first partial condenser between the first and the second columns and delivering overhead products of the first column to said first partial condenser as a vapor phase, wherein from about 2 to about 10% relative products are condensed in said partial condenser;
    (c) directing said condensed products to recycle to a feed of the first column and directing a non-condensed phase of said products comprising crude acetone to a feed of the second column;
    (d) directing a take-off of an aldehyde fraction from the second column overhead and directing of this fraction to a neutralization stage;
    (e) providing a second partial condenser between the second and the third columns and directing a take-off of the second column vapor phase as a side-draw to said second partial condenser to produce an acetone vapor phase and an acetonic liquid phase;
    (f) directing said acetone vapor phase from said second partial condenser to a third column feed, treating said acetone liquid phase with an alkali solution and returning said acetone liquid phase to said first second column and to said neutralization stage of cumene hydroperoxide cleavage products; and
    (g) removing a take-off of product acetone from the third column overhead, said product acetone having a high stability to oxidation, having a value of permanganate time from about 8 to about 70 hours.

2. The method of claim 1, further comprising the step of:
    (h) maintaining a weight ratio of liquid and vapor phases in the second partial condenser is from about 1:10 to about 1:100.

3. The method of claim 1, further comprising the step of:
    (i) recycling liquid products of the second partial condenser having unreacted aldehydes, aldols and acetone to said second column feed.

4. The method of claim 3, wherein the degree of aldols separation in the second partial condenser is higher than 90%, further comprising the step of:
    (j) directing said aldols to a neutralization stage.

5. The method of claim 1, wherein the second column comprises a feed tray, further comprising the step of:
    (k) feeding an aqueous NaOH solution to the second column above said feed tray.

6. The method of claim 5, further comprising the step of:
    (l) maintaining crude acetone/NaOH ratio on a 100% NaOH basis within the range from about 0.0036 to about 0.006 per ton of acetone.

7. The method of claim 1, further comprising the step of:
    (m) controlling permanganate time value of product acetone from about 8 to about 70 hours by selectively altering a value of liquid and vapor phases ratio of the second partial condenser.

8. The method of claim 1, further comprising the step of:
    (n) setting a reflux number at the third column is equal to about 2.5 to about 5.

9. The method of claim 1, further comprising the step of:
    (o) maintaining an atmosphere pressure in the first column and in the second column and maintaining vacuum of about 400 to about 600 Hg in the third column.

10. The method of claim 1, further comprising the step of:
    (p) maintaining different pressure is in said first and said second partial condensers.

11. The method of claim 10, wherein said step (p) comprises the step of: maintaining an atmospheric pressure in said first partial condenser and maintaining a vacuum from about 600 to about 650 Hg in said second partial condenser.

12. The method of claim 1, further comprising the step of:
(q) maintaining acetone content in a bottom of the third column equal to or below about 0.4 weight %.

13. The method of claim 1, wherein cumene concentration in said first column feed is from about 1 to about 40 weight %.

14. The method of claim 1, wherein water concentration in the first column feed is from about 2 to 15 weight %.

15. A method for rectification of product acetone with a high stability to oxidation from cumene hydroperoxide cleavage products, the method being implemented in plurality of rectification columns, said method comprising the steps of:
(a) taking off an acetone fraction overhead from an acetone and phenol streams rectification column;
(b) directing said acetone fraction through a first partial condenser to separate said acetone fraction into a condensed acetone fraction product, and an uncondensed acetone fraction product;
(c) directing condensed acetone fraction product to recycle to said acetone and phenol streams rectification column;
(d) directing said uncondensed acetone fraction product to a first product acetone rectification column having a feed tray;
(e) when the plural rectification columns exceed two columns, removing an aldehyde fraction overhead from said first product acetone rectification column and directing said aldehyde fraction to a neutralization stage;
(f) when the plural rectification columns exceed two columns, directing side-draw products from said first product acetone rectification column to a second partial condenser, to separate said side-draw products into an acetone liquid phase and an acetone vapor phase, otherwise, when the plural rectification columns are two columns, directing overhead products from said first product acetone rectification column to a second partial condenser, to separate said overhead products into an acetone liquid phase and an acetone vapor phase;
(g) simultaneously with said step (f), introducing an aqueous sodium hydroxide solution to said first product acetone rectification column above said feed tray;
(h) treating said acetone liquid phase with an alkali solution and returning said acetone liquid phase to said first product acetone rectification column and to a neutralization stage of cumene hydroperoxide cleavage products;
(i) introducing said acetone vapor phase to a second product acetone rectification column and separating said acetone vapor phase into water and product acetone; and
(j) removing said product acetone from said second product acetone rectification column.

16. The method of claim 15, wherein at said step (b) said condensed acetone fraction product comprises from about 2% to about 10% relative of said acetone fraction.

17. The method of claim 15, wherein when the plural rectification columns exceed two columns, said step (f) further comprises the step of separating said side draw products into said acetone liquid phase and said acetone vapor phase at a weight flow ratio ranging from about 1:10 to about 1:100, correspondingly, and wherein when the plural rectification columns are two columns, said step (f) further comprises the step of separating said overhead products into said acetone liquid phase and said acetone vapor phase at a weight flow ratio ranging from about 1:10 to about 1:100, correspondingly, and wherein.

18. The method of claim 15, wherein at said step (g) said aqueous sodium hydroxide is a NaOH solution delivered in a quantity from about 0.0036 ton to about 0.006 ton per one ton of acetone, wherein said quantity of NaOH is selected with reference to a required value of a permanganate test ranging from 8 to 70 hours.

19. The method of claim 15, wherein said first and said second acetone rectification columns operate under one of: atmospheric pressure and a vacuum of about 400 to about 650 mm Hg.

20. A method for rectification of product acetone with a high stability to oxidation from cumene hydroperoxide cleavage products, the method being implemented in two rectification columns, said method comprising the steps of:
(a) taking off an acetone fraction overhead from an acetone and phenol streams rectification column;
(b) directing said acetone fraction through a first partial condenser to separate said acetone fraction into a condensed acetone fraction product, and an uncondensed acetone fraction product;
(c) directing condensed acetone fraction product to recycle to said acetone and phenol streams rectification column;
(d) directing said uncondensed acetone fraction product to a product acetone rectification column having a feed tray;
(e) directing overhead products in a vapor phase from said first product acetone rectification column to a second partial condenser, to separate said overhead products into an acetone liquid phase and an acetone vapor phase and to condense said acetone vapor phase into
(f) simultaneously with said step (e), introducing an aqueous sodium hydroxide solution to said first product acetone rectification column above said feed tray;
(g) treating said acetone liquid phase with an alkali solution and returning said acetone liquid phase to said product acetone rectification column and to a neutralization stage of cumene hydroperoxide cleavage products; and
(h) removing said product acetone from said product acetone rectification column.

21. The method of claim 20, wherein at said step (b) said condensed acetone fraction product comprises from about 2% to about 10% relative of said acetone fraction.

22. The method of claim 20, wherein at said step (e) said overhead products are separated into said acetone liquid phase and said acetone vapor phase at a weight flow ratio ranging from about 1:50 to about 1:150, correspondingly.

23. The method of claim 20, wherein at said step (f) said aqueous sodium hydroxide is a NaOH solution delivered in a quantity from about 0.0036 ton to about 0.006 ton per one ton of acetone, wherein said quantity of NaOH is selected with reference to a required value of a permanganate test ranging from 4 to 40 hours.

24. The method of claim 20, wherein said product acetone rectification column operates under one of: atmospheric pressure and a vacuum of about 400 to about 650 mm Hg.

25. A rectification method, for producing high purity acetone from CHP cleavage products, implemented in a multi-stage process system, the system comprising a first, a second, and a third column, the method comprising the steps of:

(a) producing an acetone fraction from a first column overhead, the first column functioning with a reflux ratio maintained within a range of about 2–0.7;

(b) providing a total condenser between the first and the second columns and delivering overhead products of the first column to said total condenser as a vapor phase to fully condense said products therein;

(c) in accordance with said reflux ratio, directing a first portion of said condensed products to recycle to an overhead portion of the first column, and directing a second potion of said products to a feed of the second column;

(d) directing a take-off of an aldehyde fraction from the second column overhead and the direction of this fraction to a neutralization stage;

(e) providing a partial condenser between the second and the third columns and directing a take-off of the second column vapor phase as a side-draw to said partial condenser;

(f) directing said vapor phase from said partial condenser to a third column feed; and (g) removing a take-off of product acetone from the third columns as a side-draw, said product acetone having a high stability to oxidation, having a value of permanganate time from about 8 to about 70 hours.

* * * * *